United States Patent
Arthur et al.

(10) Patent No.: US 9,427,272 B2
(45) Date of Patent: *Aug. 30, 2016

(54) DEVICE FOR PERFORMING A SURGICAL PROCEDURE AND METHOD

(71) Applicant: KYPHON SARL, Neuchatel (CH)

(72) Inventors: Amy L. Arthur, Mountain View, CA (US); Mojan Goshayeshgar, Atherton, CA (US)

(73) Assignee: KYPHON SÀRL, Neuchàtel (CH)

( * ) Notice: Subject to any disclaimer, the term of this patent is extended or adjusted under 35 U.S.C. 154(b) by 496 days.

This patent is subject to a terminal disclaimer.

(21) Appl. No.: 13/803,232

(22) Filed: Mar. 14, 2013

(65) Prior Publication Data

US 2014/0276561 A1    Sep. 18, 2014

(51) Int. Cl.
    *A61B 17/88*     (2006.01)

(52) U.S. Cl.
    CPC ....... *A61B 17/8855* (2013.01); *A61B 17/8805* (2013.01); *A61B 17/8819* (2013.01)

(58) Field of Classification Search
    CPC .. A61B 19/0256; A61B 19/26; A61B 19/10; A61B 19/201; A61B 17/3403
    USPC ............................... 248/181.1, 181.2, 183.1
    See application file for complete search history.

(56) References Cited

U.S. PATENT DOCUMENTS

| | | | |
|---|---|---|---|
| 5,201,742 A * | 4/1993 | Hasson | A61B 19/201 |
| | | | 606/1 |
| 6,206,903 B1 | 3/2001 | Ramans | |
| 6,368,321 B1 * | 4/2002 | Jackson | A61B 17/7035 |
| | | | 606/270 |
| 7,166,570 B2 * | 1/2007 | Hunter | A61B 17/11 |
| | | | 514/21.92 |
| 7,749,227 B2 | 7/2010 | Lechot et al. | |
| 7,857,271 B2 | 12/2010 | Lees | |
| 9,247,980 B2 * | 2/2016 | Arthur | A61B 17/8855 |
| 2008/0167688 A1 * | 7/2008 | Fauth | A61B 17/7041 |
| | | | 606/265 |

* cited by examiner

*Primary Examiner* — Anu Ramana
(74) *Attorney, Agent, or Firm* — Martin & Ferraro LLP (57) ABSTRACT

A device including a first member extending along an axis. The first member includes an inner surface defining a cavity extending through a first surface and an opposite second surface and a side surface extending between the first and second surfaces. The inner surface defines an opening extending that is in communication with the cavity. A pivoting member is disposed in the cavity and includes an inner surface defining a passageway having a second member disposed therein. An engaging member is disposed in the opening. The pivoting member is movable between a first orientation such that the engaging member is spaced apart from the pivoting member and the pivoting member is rotatable to a selected trajectory relative to the longitudinal axis and a second orientation such that the engaging member engages the pivoting member and the second member is fixed in the selected trajectory. Methods of use are disclosed.

11 Claims, 6 Drawing Sheets

DEVICE FOR PERFORMING A SURGICAL PROCEDURE AND METHOD

TECHNICAL FIELD

The present disclosure generally relates to medical devices for the treatment of musculoskeletal structures, and more particularly to a surgical system and method that include a device configured to hold a surgical instrument while a surgical procedure is performed.

BACKGROUND

Height loss is commonly associated with fractures, such as, for example, spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing a bone void filler, such as, for example, bone cement with balloon catheter technology. The kyphoplasty procedure restores height of the collapsed spinal bone which diminishes associated back pain.

Kyphoplasty procedures may also be used to treat fractures in other areas of a patient's body, such as, for example, a distal radius of the patient. To treat a distal radius fracture using a kyphoplasty procedure, an inflatable bone tamp (IBT) is utilized. The IBT is used to percutaneously reduce comminuted, articular depressions in a controlled manner. Fracture morphologies, such as, for example, "die-punch" fractures are especially suited for correction by an IBT. IBTs are deployed to a surgical site, such as, for example, a bone defect through a working cannula. IBTs create well-defined voids. After the void is created by the IBT, the IBT is removed from the cannula and a material, such as, for example a bone void filler is delivered through the cannula and into the void. The bone void filler may be used in conjunction with percutaneous pins, ex-fixes, screws and/or plates for fracture fixation.

In conventional kyphoplasty procedures, the IBT is inserted adjacent the bone defect by inserting the IBT through a cannula. An inflatable member of the IBT is expanded to create a void in or adjacent the bone defect. After the IBT creates the void, the IBT is removed from the cannula and a bone void filler is delivered through the cannula to the void in order to at least partially fill the void. It is therefore important that the cannula be properly oriented with respect to the bone defect. In conventional kyphoplasty procedures, the cannula is held at a desired trajectory by a physician or physician's assistant, so that the IBT or bone void filler may be delivered through the cannula to a location adjacent the bone defect or void created by the IBT.

Percutaneous delivery of IBT or bone filler material through the cannula to a bone defect or bone void can be difficult. For example, the IBT or bone void filler material may get stuck in the cannula. Furthermore, the distal end of the cannula must be positioned adjacent to the bone defect or bone void to allow the IBT or bone void filler to be delivered through the cannula to the bone defect or bone void. There is often little soft tissue and/or bony anatomy to hold the cannula in a stable position during delivery of the IBT or bone filler material. To stabilize the cannula, a surgical assistant is often required to provide an extra pair of hands to hold the cannula while a surgeon delivers the IBT or the bone filler material to the bone defect or bone void through the cannula. The present disclosure provides a device that acts as a second pair of hands to hold the cannula at a fixed trajectory to ensure that the cannula is properly positioned relative to the bone defect or bone void. This disclosure describes an improvement over these prior art technologies.

SUMMARY

Accordingly, a surgical system and method for correction of a bone injury or disorder are provided. In one embodiment, in accordance with the principles of the present disclosure, the surgical system includes a device for performing a surgical procedure. The device includes a first member extending along a longitudinal axis between a first end and a second end. The first end includes an inner surface defining a cavity extending transverse to the longitudinal axis through a first surface and a second surface opposite the first surface. The first end further includes a side surface extending between the first and second surfaces. The inner surface of the first member defines an opening extending transverse to longitudinal axis through the side surface. The opening is in communication with the cavity. A pivoting member is movably disposed in the cavity and includes an inner surface defining a passageway. A second member is disposed within the passageway. An engaging member is disposed in the opening such that the pivoting member is movable between a first orientation such that the engaging member is spaced apart from the pivoting member and the pivoting member is rotatable to a selected trajectory relative to the longitudinal axis and a second orientation such that the engaging member engages the pivoting member and the second member is fixed in the selected trajectory.

In one embodiment, in accordance with the principles of the present disclosure, the surgical system includes a device comprising a first member extending along a longitudinal axis between a first end and a second end. The first end includes an inner surface defining a substantially spherical cavity extending transverse to the longitudinal axis through a first surface and a second surface opposite the first surface. The first end further includes a side surface extending between the first and second surfaces. The inner surface of the first member defines a threaded opening extending transverse to longitudinal axis through the side surface. The opening is in communication with the cavity. A pivoting member includes an inner surface defining a passageway. The pivoting member further includes a first end comprising a ball and a second end comprising a collet. The ball is disposed in the cavity and the collet is spaced apart from the cavity. A second member is disposed within the passageway and includes an inner surface defining a second passageway having an inflatable bone tamp or a bone void filler delivery tool disposed therein. A thumbscrew is disposed in the opening. The thumbscrew has a threaded outer surface configured to engage the threads of the opening. The thumbscrew includes a first end configured to engage the pivoting member and an opposite second end comprising a head configured to be rotated by hand. In some embodiments, the first end of the thumbscrew includes a material, such as, for example, a deformable material configured to facilitate engagement of the engaging member with the pivoting member. The pivoting member is movable between a first orientation such that the first end of the thumbscrew is spaced apart from the pivoting member and the pivoting member is rotatable to a selected trajectory relative to the longitudinal axis and a second orientation such that the first end of the thumbscrew engages the pivoting member and the pivoting member is fixed in the selected trajectory.

In one embodiment, in accordance with the principles of the present disclosure, a method for repairing a bone is provided. The method comprises the steps of: providing a device comprising a first member extending along a longitudinal axis between a first end and a second end, the first end including an inner surface defining a cavity extending transverse to the longitudinal axis through a first surface and a second surface opposite the first surface, the first end further including a side surface extending between the first and second surfaces, the inner surface of the first member defining an opening extending transverse to longitudinal axis through the side surface, the opening being in communication with the cavity, a pivoting member movably disposed in the cavity and including an inner surface defining a passageway, and an engaging member disposed in the opening; creating an access path to a defect in a bone; inserting the second end of the first member through the access path; inserting a second member into the passageway; rotating the pivoting member to a selected trajectory relative to the longitudinal axis such that a distal end of the second member is positioned adjacent the bone defect; and engaging the engaging member with the pivoting member such that the second member is fixed in the selected trajectory.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method include a device configured to hold a surgical instrument while performing a surgical procedure to treat a bone defect, such as, for example a fracture.

In one embodiment, the system and method include a device configured to hold a cannula having a ball and socket configuration. The ball is configured to interface with a socket in a tail of the device. A thumbscrew locks the ball into place. In some embodiments, the ball includes a collet. In some embodiments, the device is made from silicone.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, balloons that are preformed to have different sizes and shapes.

It is envisioned that the present disclosure may be employed to treat bones, such as, for example, spinal bones or arm bones. It should be understood that the present principles are applicable to any bone structures, including but not limited to bones of the spine, legs, feet, hands, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the arm, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system for holding a surgical instrument while a surgical procedure is performed. The disclosure also includes a description of related methods of employing the disclosed surgical system. Alternate embodiments are also disclosed. Reference will now be made in detail to the exemplary embodiments of the present disclosure, which are illustrated in the accompanying figures. Turning now to FIGS. 1-5, there are illustrated components of a surgical system, such as, for example, a surgical system 30 and embodiments in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open, mini-open or minimally invasive surgical technique to treat a bone defect, such as, for example a fracture. System 30 includes a tail, such as, for example, a first member 32 extending along a longitudinal axis A between a first end 34 and a second end 36. End 34 includes an inner surface 38 defining a substantially spherical cavity 40 extending transverse to the longitudinal axis through a first surface 42 and a second surface 44 opposite surface 42. It is envisioned that all or only a portion of cavity 40 may be variously configured and dimensioned, such as, for example, planar, concave, convex, hemispherical, polygonal, irregular, uniform, non-uniform, staggered, tapered, consistent or variable, depending on the requirements of a particular application. It is further envisioned that cavity 40 may be disposed at alternate orientations relative to axis A, such as, for example, perpendicular and/or other angular orientations such as acute or obtuse and/or may be offset or staggered and/or may be disposed at alternative angular orientations relative to axis A, depending on the requirements of a particular application.

End 34 includes a side surface 46 extending between surfaces 42, 44. Surface 46 defines a threaded opening 48 having a cylindrical cross sectional configuration extending transverse to axis A through surface 46 such that opening 48 is in communication with cavity 40. It is envisioned that all or only a portion of opening 48 may have alternate cross section configurations, such as, for example, oval, oblong, triangular, square, polygonal, irregular, uniform, non-uniform, offset, staggered, undulating, arcuate, variable and/or tapered, depending on the requirements of a particular application. It is further envisioned that opening 48 may be disposed at alternate orientations relative to axis A, such as, for example, perpendicular and/or other angular orientations such as acute or obtuse and/or may be offset or staggered and/or may be disposed at alternative angular orientations relative to axis A, depending on the requirements of a particular application.

End 36 includes an aperture 50 extending through surfaces 42, 44. Aperture 50 is configured to receive an engagement device, such as, for example a pin or K-wire 52 configured to fix member 32 relative to the anatomy of a patient. It is envisioned that end 36 may include one or a plurality of apertures 50. It is further envisioned that system 30 may include one or a plurality of pins/K-wires 52, corresponding to the number of apertures 50. In the embodiment shown in FIGS. 1 and 2, end 36 includes apertures 50 extending perpendicular to axis A positioned proximally of apertures 50 extending at an acute angle relative to axis A. However, it is contemplated that this configuration may be reversed. That is, the apertures 50 that extend at an acute angle relative to axis A may be positioned proximally of the apertures 50 that extend perpendicular to axis A. It is contemplated that the apertures 50 that extend at an acute angle relative to axis A may alternate with the apertures 50 that extend perpendicular to axis A. It is envisioned that apertures 50 may be disposed through angular ranges in various orientations relative to axis A, such as, for example, transverse or perpendicular and/or other angular orientations such as acute or obtuse, and/or may be offset or staggered.

In some embodiments, apertures 50 and/or pins/K-wires 52 may be rough, textured, porous, semi-porous, dimpled and/or polished to facilitate engagement between apertures 50 and pins/K-wires 52. In some embodiments, apertures 50 may comprise an elongated slot.

A pivoting member 54 is movably disposed in cavity 40 and includes an inner surface 56 defining a passageway 58. Passageway 58 has a cylindrical cross sectional configuration and a uniform diameter throughout the length of passageway 58. Member 54 includes a first end comprising a ball 60 having a substantially spherical configuration and a second end comprising a collet 62 having a cylindrical configuration. In one embodiment, shown in FIG. 5, member 54 includes a substantially spherical ball 60 and does not include a collet. Ball 60 is configured for movable disposal in cavity 40 and collet 62 is spaced apart from cavity 40 when ball 60 is dispose in cavity 40. Passageway 58 extends through both ball 60 and collet 62. It is envisioned that all or only a portion of passageway 58, ball 60 and/or collet 62 may have alternate cross section configurations, such as, for example, oval, oblong, triangular, square, polygonal, irregular, uniform, non-uniform, offset, staggered, undulating, arcuate, variable and/or tapered, depending on the requirements of a particular application.

A second member, such as, for example a cannula 64 is disposed within passageway 58. In some embodiments, surface 56 includes a deformable material 59, such as, for example, silicone or elastomer (e.g., synthetically produced butyl rubber or neoprene or a natural rubber) disposed about passageway 58 to facilitate engagement of cannula 64 with member 54. Cannula 64 includes an inner surface 66 defining a second passageway 68 configured for disposal of an inflatable bone tamp, a bone filler material or a separate delivery tool configured to deliver bone filler material in order to deliver the inflatable bone tamp or the bone filler material to a surgical site, such as, for example a bone defect. Passageway 68 has a cylindrical cross sectional configuration and a uniform diameter throughout the length of passageway 68. It is envisioned that all or only a portion of passageway 68 may have alternate cross section configurations, such as, for example, oval, oblong, triangular, square, polygonal, irregular, uniform, non-uniform, offset, staggered, undulating, arcuate, variable and/or tapered, depending on the requirements of a particular application.

An engaging member, such as, for example, a thumbscrew 70 is disposed in opening 48. Thumbscrew 70 is configured to engage member 54 to fix member 54 relative to member 32 and includes a threaded outer surface 72 configured to engage the threads in opening 48 to engage thumbscrew 70 with member 32. However, it is envisioned that thumbscrew 70 may engage member 32 in alternate fixation configurations, such as, for example, friction fit, pressure fit, locking protrusion/recess, locking keyway and/or adhesive.

Thumbscrew 70 includes a first end 74 configured to engage member 54 and an opposite second end 76 comprising an enlarged head 78 configured to be rotated by hand. End 74 includes a planar face 80 extending parallel to axis A configured to engage member 54 to prevent member 54 from moving relative to member 32. In some embodiments, a deformable material, such as, for example, silicone or elastomer (e.g., synthetically produced butyl rubber or neoprene or a natural rubber) is disposed on face 80 to facilitate engagement of thumbscrew 70 with member 54.

Figure 1:
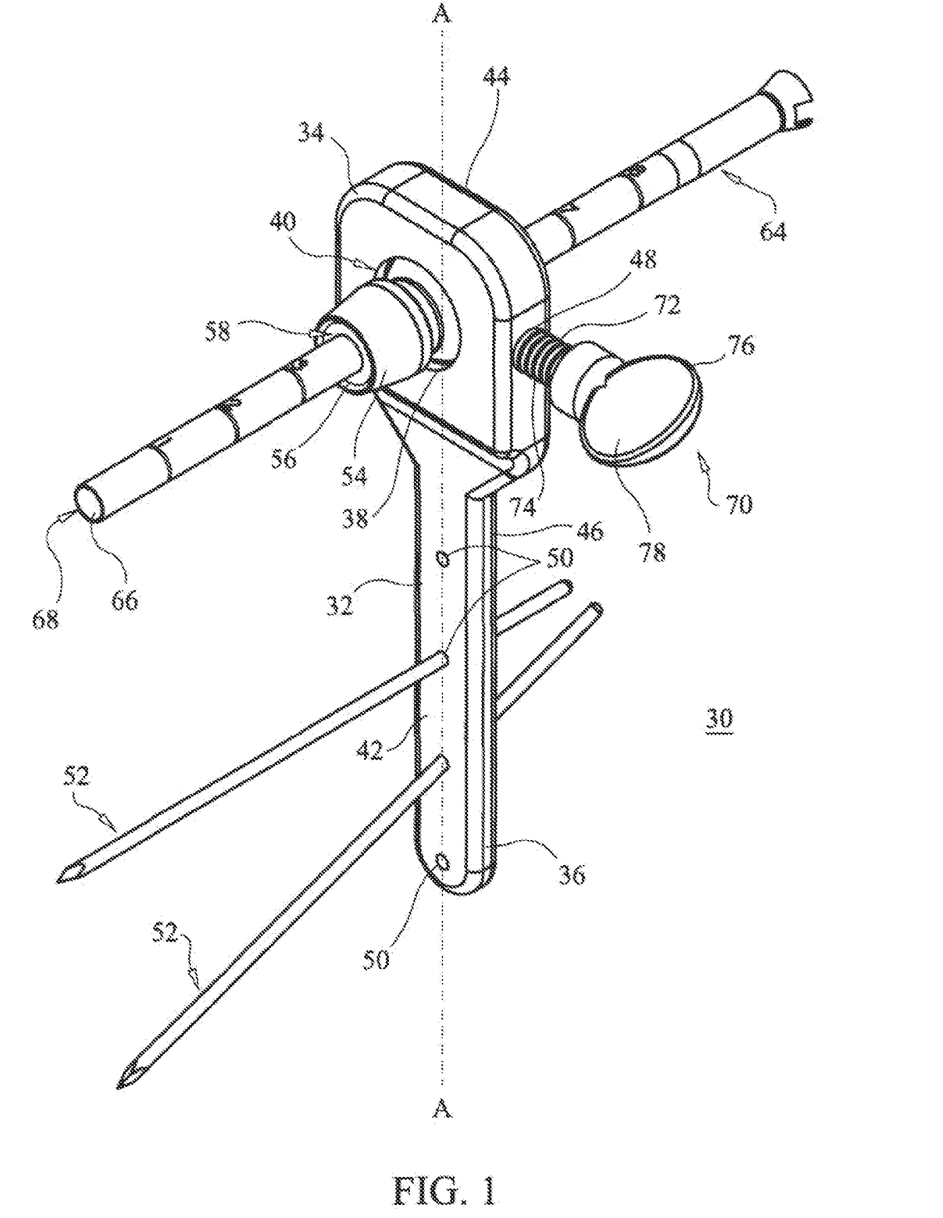
FIG. 1 is a perspective view of one embodiment of components of a system in accordance with the principles of the present disclosure.
Figure 2:
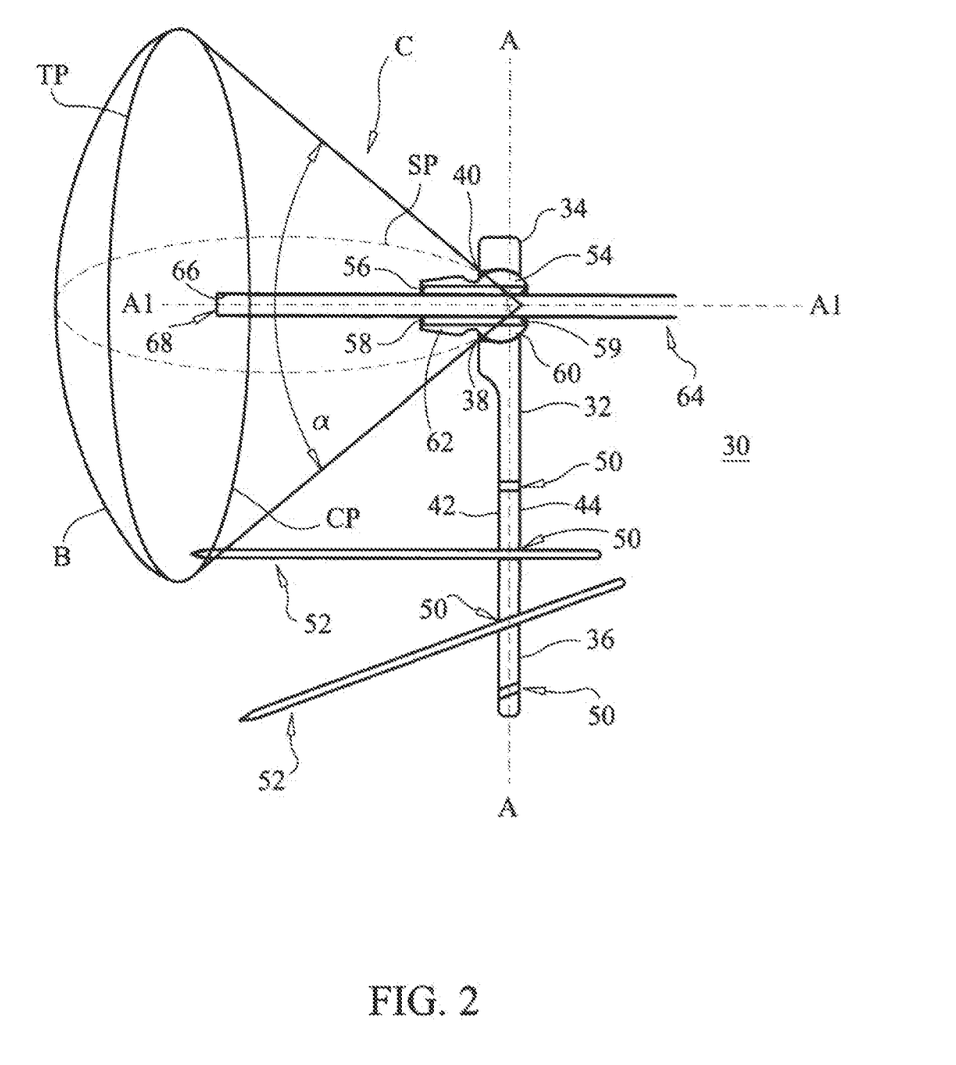
FIG. 2 is a side, cross sectional view of components of the system shown in FIG. 1.
Figure 3:
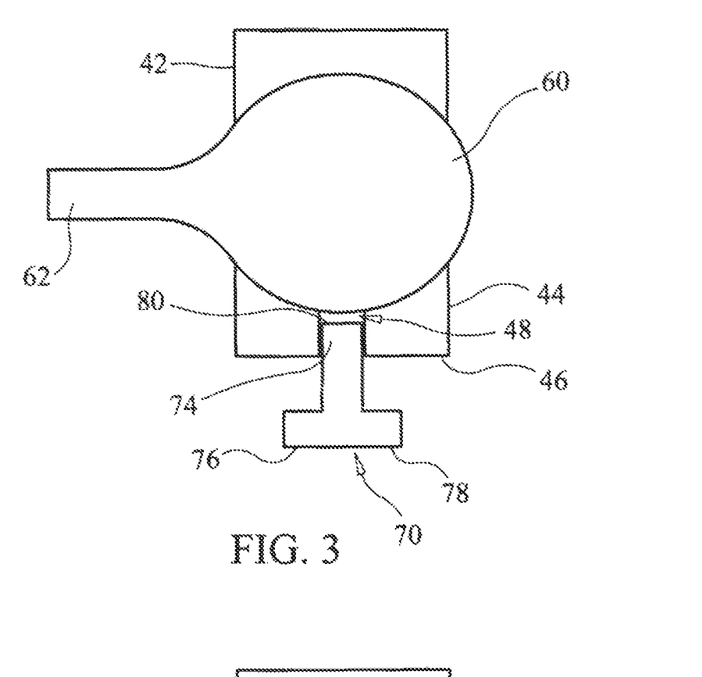
FIG. 3 is a top, cross sectional view of components of the system shown in FIG. 1.
Figure 4:
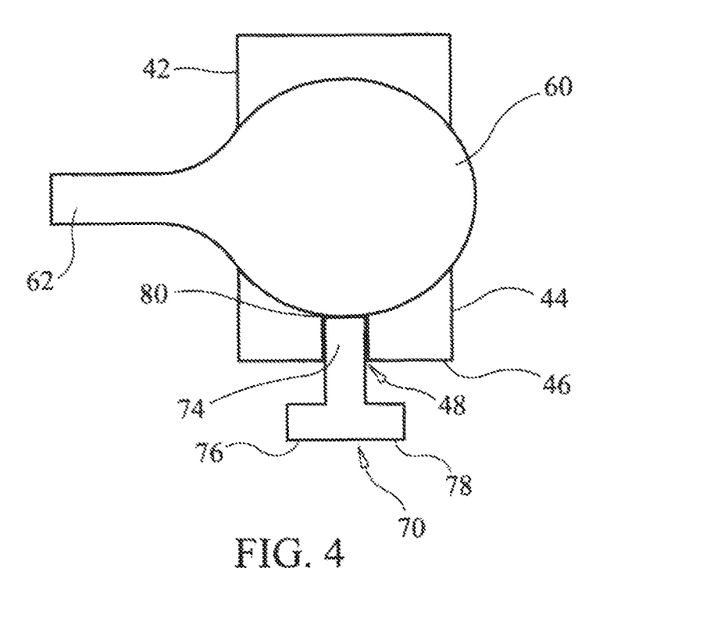
FIG. 4 is a top, cross sectional view of components of the system shown in FIG. 1.
Figure 5:
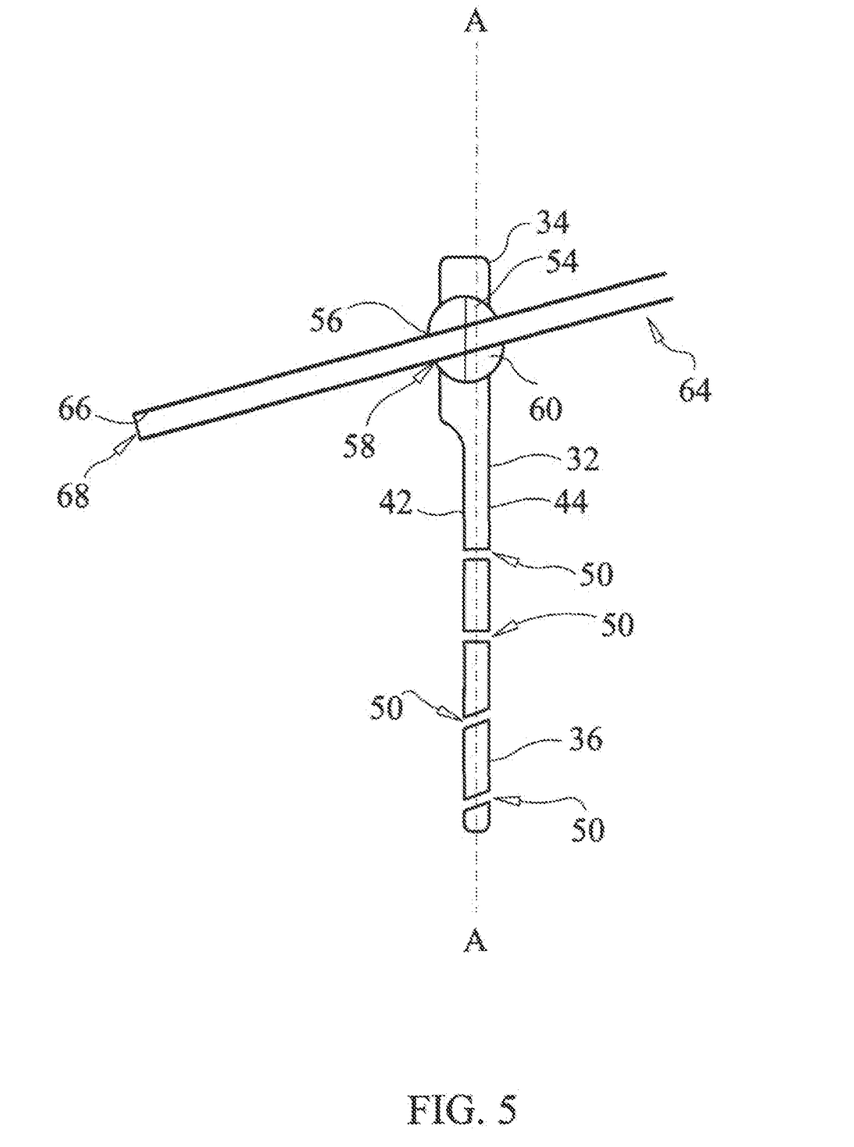
FIG. 5 is a side, cross sectional view of components of a system in accordance with the principles of the present disclosure.

Member 54 is movable between a first orientation such that end 74 is spaced apart from member 54, as shown in FIG. 3, and member 54 is rotatable to a selected trajectory relative to axis A and a second orientation such that end 74 engages member 54, as shown in FIG. 4, to fix member 54 in the selected trajectory. When member 54 is in the first orientation, passageway 58 is rotatable to a selected angle through and within angular range a relative to axis a in a plurality of planes that lie in a cone configuration C, as shown in FIG. 2. The area and/or volume defined by cone C, which includes the configuration disposed between a transverse axis A1 and a circular base B, is defined by the range of motion of passageway 58 axis A1. The plurality of planes includes a locus of all straight line segments that join axis A1 and base B. For example, passageway 58 is separately rotatable to a selected angle within angular range a in each plane corresponding to a particular straight line segment that lies in cone configuration C. It is contemplated that passageway 58 may rotatable through the individual diameters, chords, section and/or radii of base b and/or other portions of cone C. In one embodiment, passageway 58 is rotatable to a selected angle within angular range a in a sagittal plane (SP), corresponding to a particular plane that lies in cone C. In one embodiment, passageway 58 is rotatable to a selected angle within angular range a in a transverse plane (TP), corresponding to a particular plane that lies in cone C. In one embodiment, passageway 58 is rotatable to a selected angle within angular range a in a coronal plane (CP), corresponding to a particular plane that lies in cone C.

Figure 6:
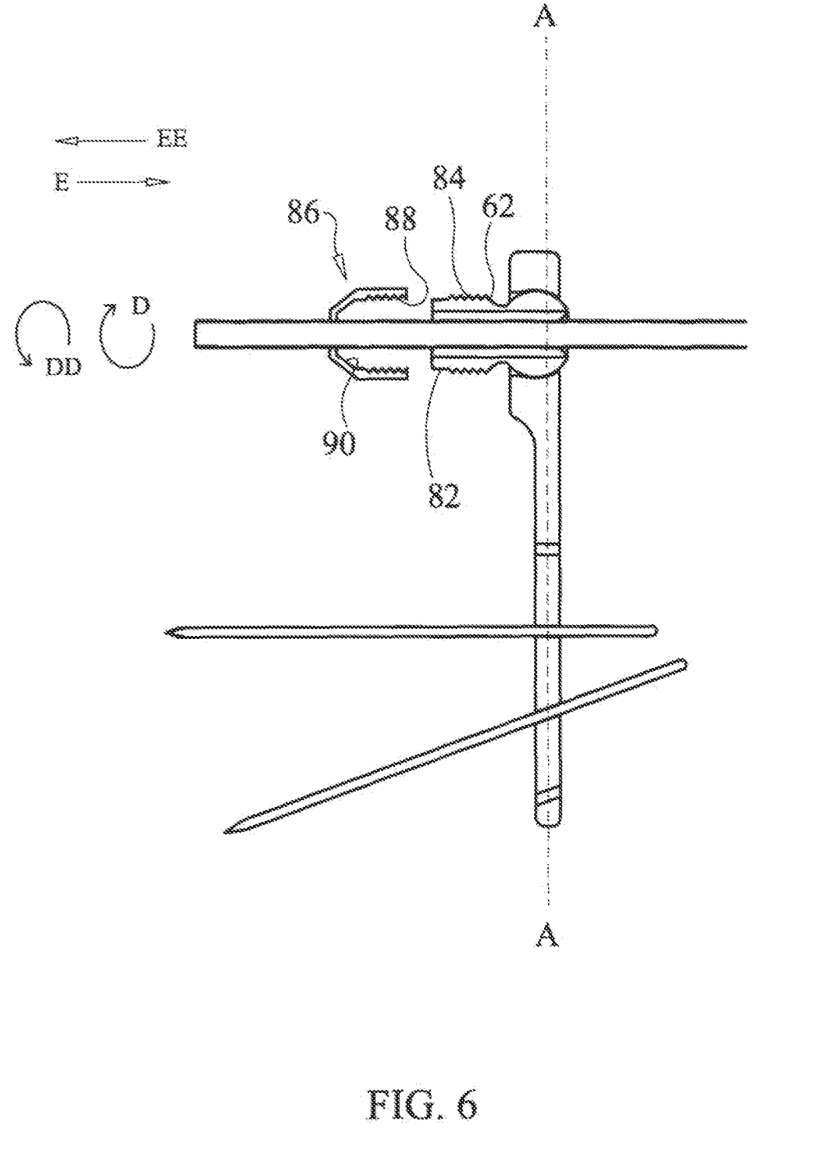
FIG. 6 is a side, cross sectional view of components of a system in accordance with the principles of the present disclosure, with a cap in a first orientation.
Figure 7:
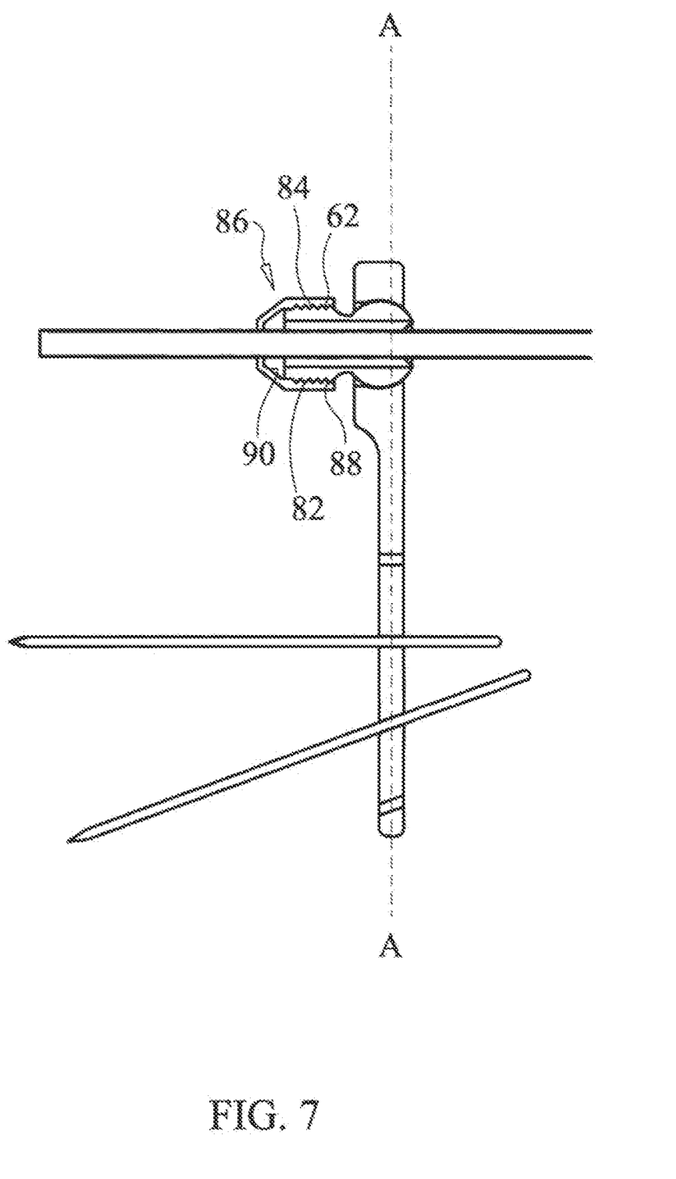
FIG. 7 is a side, cross sectional view the system shown in FIG. 6, with the cap in a second orientation.

In one embodiment, shown in FIGS. 6 and 7, collet 62 includes an outer surface having a uniform diameter along the length of collet 62. The outer surface of collet 62 includes an unthreaded first portion 82 and a threaded second portion 84 extending from portion 82. System 30 includes a cap 86 includes a first end having a threaded inner surface 88 and a second end having with an angled inner surface 90 that is free of threads. Threaded inner surface 88 is configured to engage portion 84 to engage cap 86 with collet 62. As threaded inner surface 88 engages portion 84, cap 86 is rotated in the direction shown by arrow D or arrow DD such that cap 86 translates relative to collet 86 in the direction shown by arrow E. As cap 86 translates in the direction shown by arrow E, angled inner surface 90 engages portion 82 causing inner surface 56 to engage cannula 64. Because surface 90 is angled, rotation of cap 86 in the direction shown by arrow D or arrow DD allows for incremental tightening of surface 56 about cannula 64 such that a restrictive force applied to cannula 64 can be adjusted by altering the amount of rotation of cap 86. When portion 84 is fully threaded with portion 88, cannula 64 becomes fixed relative to collet 62. That is, cap 86 is movable between a first orientation such that threaded inner surface 88 is spaced apart from portion 84, as shown in FIG. 6 and cannula 64 is movably disposed within passageway 58 and a second orientation such that threaded inner surface 88 engages portion 84 and cannula 64 is fixed within passageway 58.

In assembly, operation and use, system 30 is employed with a surgical procedure, such as, for a correction or treatment of a bone defect, such as, for example, a fracture. It is contemplated that one or all of the components of system 30 can be delivered or implanted as a pre-assembled device or can be assembled in situ. System 30 may be completely or partially revised, removed or replaced. For example, system 30 can be employed with a surgical correction treatment of an applicable condition or injury of an affected portion of a patient, such as, for example, a distal radius or a vertebra. It is envisioned that system 30 may also be used to treat other affected portions of the patient, such as, for example, a calcaneus bone, bones of the feet or hands, bones of the legs, etc.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 30 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 30 is determined according to the configuration, dimension and location of a selected section of the bone fracture and the requirements of a particular application.

An incision is made in the body of a patient and a cutting instrument (not shown) creates a surgical pathway for implantation of components of system 30. This may include the use of a cannula or other device. A preparation instrument (not shown) can be employed to prepare tissue surfaces, as well as for aspiration and irrigation of a surgical region according to the requirements of a particular surgical application.

Pins/K-wires 52 are positioned within through apertures 50 and are disposed in the anatomy of the patient, such as, for example, tissue, to fix or stabilize member 32 relative to the anatomy of the patient, with cannula 64 positioned within passageway 58. Member 32 is stabilized with pins/K-wires 52.

In embodiments, that include cap 86, threaded inner surface 88 is aligned with portion 84. Cap 86 is rotated in the direction shown by arrow D or arrow DD such that threaded inner surface 88 engages portion 84 and cap 86 translates relative to collet 62 in the direction shown by arrow E. Cap 86 is translated in the direction shown by arrow E until angled inner surface 90 engages portion 82 causing inner surface 56 to engage cannula 64 such that cannula 64 is fixed relative to member 54. Member 54 is then rotatable to a selected trajectory relative to axis A such that cannula 64 is positioned adjacent the bone disorder. Thumbscrew 70 is translated within opening 48 until end 74 engages member 54 to fix member 54 in the selected trajectory.

An inflatable bone tamp may then be delivered through cannula 64 to a location adjacent the bone disorder or defect. The inflatable bone tamp may then be expanded to create a cavity or void in the bone by delivering a material, such as, for example, saline, a contrast solution or compressed air into an expandable member of the inflatable bone tamp, such as, for example, a balloon, to move the balloon from an unexpanded configuration to an expanded configuration. As the balloon moves from the unexpanded configuration to the expanded configuration, the balloon creates a void in the bone having the defect or disorder. Member 54 maintains cannula 64 in a stabilized orientation with respect to the body such that a single practitioner can insert the inflatable bone tamp through cannula 64 and operate the inflatable bone tamp in a steady manner. That is, cannula 64 remains at the selected trajectory such that a distal end of cannula 64 is positioned adjacent the bone defect, without the need for a physician or physician's assistant to hold cannula 64.

After the void is formed in the bone, the inflatable bone tamp is removed from cannula 64. Bone filler material is then delivered through cannula 64 or a separate delivery tool configured to deliver bone filler material disposed in passageway 58 and into the void so as to at least partially fill the void and realign fragments of the fracture and/or elevate collapsed bone to its proper height. Member 54 maintains cannula 64 in a stabilized orientation with respect to the body such that a single practitioner can administer the bone filler material in a steady manner. That is, cannula 64 remains at the selected trajectory such that a distal end of cannula 64 is positioned adjacent the bone defect, without the need for a physician or physician's assistant to hold cannula 64. It is envisioned that the bone filler material may include autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables.

In one embodiment, system 30 includes an agent, which may be disposed, packed or layered within, on or about the components and/or surfaces of the components of system 30, such as, for example. It is envisioned that the agent may include bone growth promoting material, such as, for example, bone graft to enhance fixation of the fixation elements with the bone in need of repair. It is further contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 30 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these embodiments, which, nevertheless, fall within the spirit of the present disclosure, whose scope is defined by the claims set forth below.

What is claimed is:

1. A device for holding a surgical tool comprising:
    a first member extending along a longitudinal axis between a first end and a second end, the first end including an inner surface defining a cavity extending transverse to the longitudinal axis through a first surface and a second surface opposite the first surface, the first end further including a side surface extending between the first and second surfaces, the inner surface of the first member defining an opening extending transverse to the longitudinal axis through the side surface, the opening being in communication with the cavity;

a pivoting member movably disposed in the cavity and including an inner surface defining a passageway, the passageway defining a transverse axis, the transverse axis being substantially transverse to the longitudinal axis;

a cannula disposed within the passageway; and an engaging member disposed in the opening, wherein the pivoting member is movable between a first orientation wherein the engaging member is spaced apart from the pivoting member and the pivoting member is rotatable to a selected trajectory relative to the longitudinal axis, and a second orientation wherein the engaging member engages the pivoting member, the engaging member fixing the pivoting member in the selected trajectory, the transverse axis through the passageway being rotatable about a fixed pivot point in the passageway through and within an angular range relative to the longitudinal axis such that movement throughout the angular range is within a cone configuration; and wherein the passageway is rotatable to a selected angle relative to the longitudinal axis corresponding to at least one straight line segment lying within the cone configuration.

2. A device according to claim 1, wherein the cannula includes an inner surface defining a second passageway, the second passageway having disposed therein one of an inflatable bone tamp and a delivery tool, the delivery tool being configured to deliver the inflatable bone tamp.

3. A device according to claim 1, wherein the cannula includes an inner surface defining a second passageway, the second passageway having disposed therein one of a bone void filler material, and a delivery tool, the delivery tool being configured to deliver the bone void filler material.

4. A device according to claim 1, wherein the cavity is substantially spherical.

5. A device according to claim 1, wherein the engaging member is a thumbscrew.

6. A device according to claim 1, wherein the engaging member includes a first end configured to engage the pivoting member and an opposite second end comprising a head configured to be rotated by hand.

7. A device according to claim 1, wherein the engaging member includes a first end configured to engage the pivoting member and an opposite second end comprising a head configured to be rotated by hand, the first end of the engaging member including a deformable material configured to facilitate engagement of the engaging member with the pivoting member.

8. A device according to claim 1, wherein the pivoting member is substantially spherical.

9. A device according to claim 1, wherein the opening and an outer surface of the engaging member are threaded, the threads of opening being configured to engage the threads of the engaging member.

10. A device according to claim 1, wherein the pivoting member includes a first end comprising a ball and a second end comprising a collet, the ball being configured for removable disposal in the cavity and the collet being spaced apart from the cavity at least when the ball is in the cavity.

11. A device for holding a surgical tool comprising:

a first member extending along a longitudinal axis between a first end and a second end, the first end including an inner surface defining a substantially spherical cavity extending transverse to the longitudinal axis through a first surface and a second surface opposite the first surface, the first end further including a side surface extending between the first and second surfaces, the inner surface of the first member defining a threaded opening extending transverse to longitudinal axis through the side surface, the opening being in communication with the cavity;

a pivoting member including an inner surface defining a passageway, the pivoting member including a first end comprising a ball, a second end comprising a collet, the ball being disposed in the cavity, and the collet being spaced apart from the cavity, the passageway defining a transverse axis, the transverse axis being substantially transverse to the longitudinal axis;

a second member disposed within the passageway, the second member including an inner surface defining a second passageway, the second passageway being configured to have one of an inflatable bone tamp and a bone void filler disposed therein; and a thumbscrew disposed in the opening, the thumbscrew having a threaded outer surface configured to engage the threads of the opening, the thumbscrew including a first end configured to engage the pivoting member and an opposite second end comprising a head configured to be rotated by hand, the first end of the thumbscrew including a deformable material configured to facilitate engagement of the engaging member with the pivoting member, wherein the pivoting member is movable between a first orientation wherein the first end of the thumbscrew is spaced apart from the pivoting member and the pivoting member is rotatable to a selected trajectory relative to the longitudinal axis, and a second orientation wherein the first end of the thumbscrew engages the pivoting member fixing the pivoting member in the selected trajectory, the transverse axis through the passageway being rotatable about a fixed point in the passageway through and within an angular range relative to the longitudinal axis such that movement throughout the angular range is within a cone configuration; and wherein the passageway is rotatable to a selected angle relative to the longitudinal axis corresponding to at least one straight line segment lying within the cone configuration.

\* \* \* \* \*